United States Patent
Wang et al.

(10) Patent No.: US 8,957,266 B2
(45) Date of Patent: Feb. 17, 2015

(54) PROCESS FOR MAKING SATURATED HYDROCARBONS AND THE USE THEREOF

(75) Inventors: Kun Wang, Bridgewater, NJ (US); Margaret May-Som Wu, Skillman, NJ (US); David Lawrence Stern, Fairfax Station, VA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 745 days.

(21) Appl. No.: 12/660,815

(22) Filed: Mar. 4, 2010

(65) Prior Publication Data

US 2010/0234654 A1 Sep. 16, 2010

Related U.S. Application Data

(60) Provisional application No. 61/210,045, filed on Mar. 13, 2009.

(51) Int. Cl.
 *C07C 1/213* (2006.01)
 *C07C 29/149* (2006.01)
 *C10M 105/04* (2006.01)

(52) U.S. Cl.
 CPC ........... *C07C 29/149* (2013.01); *C10M 105/04* (2013.01); *C10G 2400/10* (2013.01); *C10M 2203/0206* (2013.01);
 (Continued)

(58) Field of Classification Search
 CPC .......... C07C 1/2078; C07C 9/14; C07C 9/22; C07C 2529/89
 USPC ................. 585/254, 502, 533, 638, 310, 733; 562/509; 208/19
 See application file for complete search history.

(56) References Cited

U.S. PATENT DOCUMENTS 3,114,695 A * 12/1963 Rabo et al. ...................... 208/46
3,367,952 A * 2/1968 Arlt, Jr. ............................. 530/233

(Continued)

FOREIGN PATENT DOCUMENTS

| JP | 51-31241 | 12/1965 |
| JP | 76031241 B | 9/1976 |
| WO | WO 2007/068800 | 6/2007 |

OTHER PUBLICATIONS

Busca, "Acid Catalysts in Industrial Hydrocarbon Chemistry" in Chem. Rev. 2007, 107, 5366-5410—Oct. 2007.*
M. J. A. M. Den Otter, "The Dimerization of Oleic Acid with Montmorillonite Catalyst I: Important Process Parameters; Some Main Reactions", *Fette, Seifen, Anstrichmittel*, 1970, 667-673.

(Continued)

*Primary Examiner* — In Suk Bullock
*Assistant Examiner* — Bradley Etherton
(74) *Attorney, Agent, or Firm* — Robert A. Migliorini

(57) ABSTRACT

Provided are processes for making one or more unsaturated oligomeric acids and one or more saturated hydrocarbons. In one form, a process for making one or more saturated hydrocarbons includes oligomerizing one or more unsaturated carboxylic acids having from 4 to 38 carbon atoms in the presence of a molecular sieve catalyst to form one or more unsaturated oligomeric acids including less than 90% by weight of cyclic oligomers, and hydrogenating the one or more unsaturated oligomeric acids via contact with hydrogen in the presence of a hydrogenation catalyst to form one or more saturated hydrocarbons. The oligomerizing of unsaturated fatty acids is from renewable biological sources to form dimer acids. The one or more saturated hydrocarbons are useful as lubricant base oils.

38 Claims, 11 Drawing Sheets

(52) U.S. Cl.
CPC .... *C10N 2220/022* (2013.01); *C10N 2220/023* (2013.01); *C10N 2230/74* (2013.01); *C10N 2270/00* (2013.01)
USPC .......................... 585/254; 585/310; 585/733

(56) References Cited

U.S. PATENT DOCUMENTS

| | | | | |
|---|---|---|---|---|
| 5,079,204 | A | * | 1/1992 | Lee ............................... 502/104 |
| 5,659,106 | A | * | 8/1997 | Frey et al. ..................... 585/803 |
| 5,951,963 | A | | 9/1999 | He et al. |
| 2007/0131579 | A1 | | 6/2007 | Koivusalmi et al. |
| 2007/0191662 | A1 | * | 8/2007 | Oikarinen et al. ............ 585/533 |
| 2010/0018108 | A1 | * | 1/2010 | Miller ............................ 44/308 |

OTHER PUBLICATIONS

H. W. G. Heynen, W. H. M. J. Van Opstal, M. J. A. M. Den Otter, "The Catalytic Dimerization of Oleic Acid in a Continuous Flow Reactor", *Fette, Seifen, Anstrichmittel*, 1972, 677-681.

P. Tolvanen, P. Maki-Arvela, N. Kumar, K. Eranen, R. Sjoholm, J. Hemming, B. Holmbom, T. Salmi, D. Y. Murzin, "Thermal and Catalytic Oligomerization of Fatty Acids", *Applied Catalysis A; General*, 2007, 330, 1-11.

M. Snare, I, Kubickova, P. Maki-Arvela, K. Eranen, D. Y. Murzin, "Heterogeneous Catalytic Deoxygenation of Stearic Acid for Production of Biodiesel", *Ind. Eng. Chem. Res.*, 2006, 5708-5715.

* cited by examiner

PROCESS FOR MAKING SATURATED HYDROCARBONS AND THE USE THEREOF

CROSS-REFERENCE TO RELATED APPLICATIONS

This is a Non-Provisional Application that claims priority to U.S. Provisional Application No. 61/210,045 filed Mar. 13, 2009, which is herein incorporated by reference in its entirety.

FIELD

The present disclosure relates to a process for making saturated hydrocarbons useful as lube base stocks. The present disclosure further relates to uses of such saturated hydrocarbons.

BACKGROUND

Base oils are commonly used for the production of lubricants, such as lubricating oils for automotives, industrial lubricants and lubricating greases. They are also used as process oils, white oils, metal working oils and heat transfer fluids. Finished lubricants consist of two general components, lubricating base oil and additives. Lubricating base oil is the major constituent in these finished lubricants and contributes significantly to the properties of the finished lubricant. In general, a few lubricating base oils are used to manufacture a wide variety of finished lubricants by varying the mixtures of individual lubricating base oils and individual additives.

According to the American Petroleum Institute (API) classifications, base oils are categorized in five groups based on their saturated hydrocarbon content, sulfur level, and viscosity index (Table 1). Lube base oils are typically produced in large scale from non-renewable petroleum sources. Group I, II, and III base stocks are all derived from crude oil via extensive processing, such as solvent extraction, solvent or catalytic dewaxing, and hydroisomerization. Group III base oils can also be produced from synthetic hydrocarbon liquids obtained from natural gas, coal or other fossil resources. Group IV base stocks, the polyalphaolefins (PAO), are produced by oligomerization of alpha olefins, such as 1-decene. Group V base oils include everything that does not belong to Groups I-IV, such as naphthenics, polyalkylene glycols (PAG), and esters.

TABLE 1

| API classification | Group I | Group II | Group III | Group IV | Group V |
| --- | --- | --- | --- | --- | --- |
| % Saturates | <90 | ≥90 | ≥90 | Poly-alphaolefins (PAO) | All others not belonging to group I-IV |
| % S | >0.03 | ≤0.03 | ≤0.03 | | |
| Viscosity Index (VI) | 80-120 | 80-120 | ≥120 | | |

The automotive industry has been using lubricants and thus base oils with improved technical properties for a long time. Increasingly, the specifications for finished lubricants require products with excellent low temperature properties, high oxidation stability and low volatility. Generally lubricating base oils are base oils having kinematic viscosity of about 3 cSt or greater at 100° C. (Kv100); pour point (PP) of about −12° C. or less; and viscosity index (VI) about 90 or greater. In general, high performance lubricating base oils should have a Noack volatility no greater than current conventional Group I or Group II light neutral oils. Currently, only a small fraction of the base oils manufactured today are able to meet these demanding specifications.

For environmental, economical, and regulatory reasons, it is of interest to produce fuels, chemicals, and lube oils from renewable sources of biological origin. So far only esters of renewable and biological origin have been used in applications such as refrigeration compressor lubricants, bio-hydraulic oils and metal working oils. In automotive and industrial lubricants, esters from biological sources are used in very small fractions as additives due to technical problems as well as their high prices. For example, ester base oils can hydrolyze readily producing acids, which in turn cause corrosion on lubricating systems.

In contrast, base oils consisting of hydrocarbons from biological sources do not have those technical problems associated with esters from same sources. Most common biological sources for hydrocarbons are natural oils, which can be derived from plant sources such as canola oil, castor oil, sunflower seed oil, rapeseed oil, peanut oil, soy bean oil, and tall oil, or derived from animal fats. The basic structural unit of natural oils and fats is a triglyceride, which is an ester of glycerol with three fatty acid molecules having the structure below:

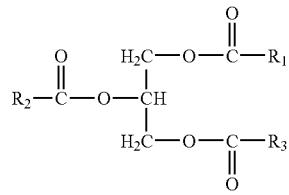

wherein $R_1$, $R_2$, and $R_3$ represent $C_4$-$C_{30}$ hydrocarbon chains. Fatty acids are carboxylic acids containing long linear hydrocarbon chains. Lengths of the hydrocarbon chains most commonly are 18 carbons ($C_{18}$). $C_{18}$ fatty acids are typically bonded to the middle hydroxyl group of glycerol. Typical carbon numbers of the fatty acids linked to the two other hydroxyl groups are even numbers, being between $C_{14}$ and $C_{22}$. Fatty acid composition of biological origin may vary considerably among feed-stocks from different sources. While several double bonds may be present in fatty acids, they are non-conjugated (with at least one —$CH_2$— unit between the double bonds). With respect to configuration, the double bonds of natural fatty acids are mostly of cis form. As the number of the double bonds increase, they are generally located at the free end of the chain. Lengths of hydrocarbon chains and numbers of double bonds depend on the various plant or animal fats or waxes serving as the source of the fatty acid. Animal fats typically contain more saturated fatty acids than unsaturated fatty acids. Fatty acids of fish oil contain high amounts of double bonds, and the average length of the hydrocarbon chains is higher compared to fatty acids of plant oils and animal fats.

Prior to processing, starting materials of biological origin are commonly pretreated with any suitable known methods such as thermally, mechanically for instance by means of shear forces, chemically for instance with acids or bases, or physically with radiation, distillation, cooling, or filtering. The purpose of said chemical and physical pretreatments is to remove impurities interfering with the process or poisoning the catalysts, and reduce unwanted side reactions.

In a hydrolysis treatment, oils and fats react with water yielding free fatty acids and glycerol as the product. Three main processes for the industrial production of fatty acids are known: vapor splitting of triglycerides under high pressure, basic hydrolysis, and enzymatic hydrolysis. In the vapor splitting process, the hydrolysis of triglycerides using steam is carried out at temperatures between 100 and 300° C., under a pressure of 1-10 MPa, preferable conditions being from 250 to 260° C. and from 4 to 5.5 MPa. Metal oxides like zinc oxide may be added as the catalyst to accelerate the reaction.

The unsaturated fatty acids obtained from hydrolysis of natural oils can be dimerized to form dimers of unsaturated fatty acids. A variety of dimerization processes have been described. For example, in Kirk-Othmer: Encyclopedia of Chemical Technology, $3^{rd}$ Ed., vol. 7, Dimer acids, p. 768, a method is presented for producing dimeric acids from unsaturated carboxylic acids with a radical reaction using a cationic catalyst, the reaction temperature being 230° C. In addition to acyclic unsaturated dimeric acid as the main product, mono- and bi-cyclic dimers are also formed. In Koster R. M. et al., Journal of Molecular Catalysis A: Chemical 134 (1998) 159-169, oligomerization of carboxylic acids, carboxylic acid methyl esters, and synthetic alcohols and olefins is described, yielding corresponding dimers.

The oxygen atoms in carboxylic acids can be removed in the form of CO (decarbonylation), $CO_2$ (decarboxylation), or $H_2O$ (deoxygenation). Processes wherein the oxygen of a carboxylic acid or ester is removed are known. Decarboxylation of fatty acids removes $CO_2$ and results in hydrocarbons with one carbon atom less than the original molecule. The feasibility of decarboxylation varies greatly with the type of carboxylic acid used as the starting material. Activated carboxylic acids containing electron-withdrawing groups in the position alpha or beta with respect to the carboxylic group lose carbon dioxide readily at slightly elevated temperatures. In this case, the RC—COOH bond is weakened by the electron-withdrawing group on the carbon chain. With other types of carboxylic acids, the RC—COOH bond is strong and cleavage of carbon dioxide is difficult. A suitable catalyst is required for this reaction. For example, in Maier, W. F. et al., Chemische Berichte (1982), 115(2), 808-812, hydrocarbons are produced from carboxylic acids using heterogeneous $Ni/Al_2O_3$ and $Pd/SiO_2$ catalysts at 180° C. under hydrogen atmosphere. Further examples of decarboxylation and hydrogenation of oxygen containing compounds are disclosed in Laurent, E., Delmon, B.: Applied Catalysis, A: General (1994), 109(1), 77-96, and 97-115, wherein pyrolysis oils derived from biomass were subjected to hydrogenation using sulfided $CoMo/\gamma-Al_2O_3$ and $NiMo/\gamma-Al_2O_3$ catalysts at 260-300° C., under a hydrogen pressure of 7 MPa.

In published U.S. Publication No. 2007/0131579, processes for converting unsaturated carboxylic acids to saturated hydrocarbons are described. The processes employ steps of: (a) oligomerization of unsaturated fatty acids forming dimer acids; (b) pre-hydrogenation to remove the C═C double bond(s); (c) de-oxygenation of the dimer acids in the form of decarboxylation and/or decarbonylation; and (d) optional hydrofinishing to remove double bonds and aromatics. Once the dimer acids are formed, tedious three steps are required in these disclosed processes to generate saturated hydrocarbons. Furthermore, this patent publication discloses a preferred product composition containing 20-90% naphthenes.

JP 76031241B discloses insulating oils formed by dimerization/trimerization of unsaturated fatty acids followed by hydrogenation. Oxygen atoms are removed in the form of water via hydrogenation, which requires two steps of hydrogenation to achieve.

With recent developments in biodiesel production, unsaturated fatty acids and their esters are increasingly available. Therefore it is desirable to take advantage of the renewable feed-stocks, thus saving non-renewable petroleum raw materials. Despite of the above teaching in the art, there is an need for an alternative and simpler process for producing saturated hydrocarbons from starting materials of biological origin, and to avoid the problems associated with the solutions disclosed in the prior art.

SUMMARY

According to the present disclosure, there are provided processes for making one or more unsaturated oligomeric acids and one or more saturated hydrocarbons.

The processes disclosed herein include: (1) oligomerization of unsaturated fatty acids from biological sources forming dimer acids; and then optionally (2) hydrogenation of the dimer acids in a substantially single step for obtaining saturated hydrocarbons.

In one form of the present disclosure, a process for making one or more unsaturated oligomeric acids comprises oligomerizing one or more unsaturated carboxylic acids having from 4 to 38 carbon atoms in the presence of a catalyst, wherein the catalyst is a molecular sieve, and wherein the one or more unsaturated oligomeric acids comprise less than 90% by weight of cyclic oligomers.

In another form of the present disclosure, a process for making one or more saturated hydrocarbons comprises oligomerizing one or more unsaturated carboxylic acids having from 4 to 38 carbon atoms in the presence of a molecular sieve catalyst to form one or more unsaturated oligomeric acids including less than 90% by weight of cyclic oligomers, and hydrogenating the one or more unsaturated oligomeric acids via contact with hydrogen in the presence of a hydrogenation catalyst to form one or more saturated hydrocarbons.

Further according to the present disclosure, there is provided saturated hydrocarbons made by hydrogenation of dimer acids from biological sources in a substantially single step.

Further according to the present disclosure, there is provided a method for lubricating a device or apparatus of moving and/or interacting mechanical parts, components, or surfaces requiring lubrication. The method has the step of applying to the apparatus or machine an amount of a lubricant taking the form of the saturated hydrocarbons produced by the processes of this disclosure.

DESCRIPTION OF THE DRAWINGS

To assist those of ordinary skill in the relevant art in making and using the subject matter hereof, reference is made to the appended drawings, wherein.

DETAILED DESCRIPTION

Figure 1:
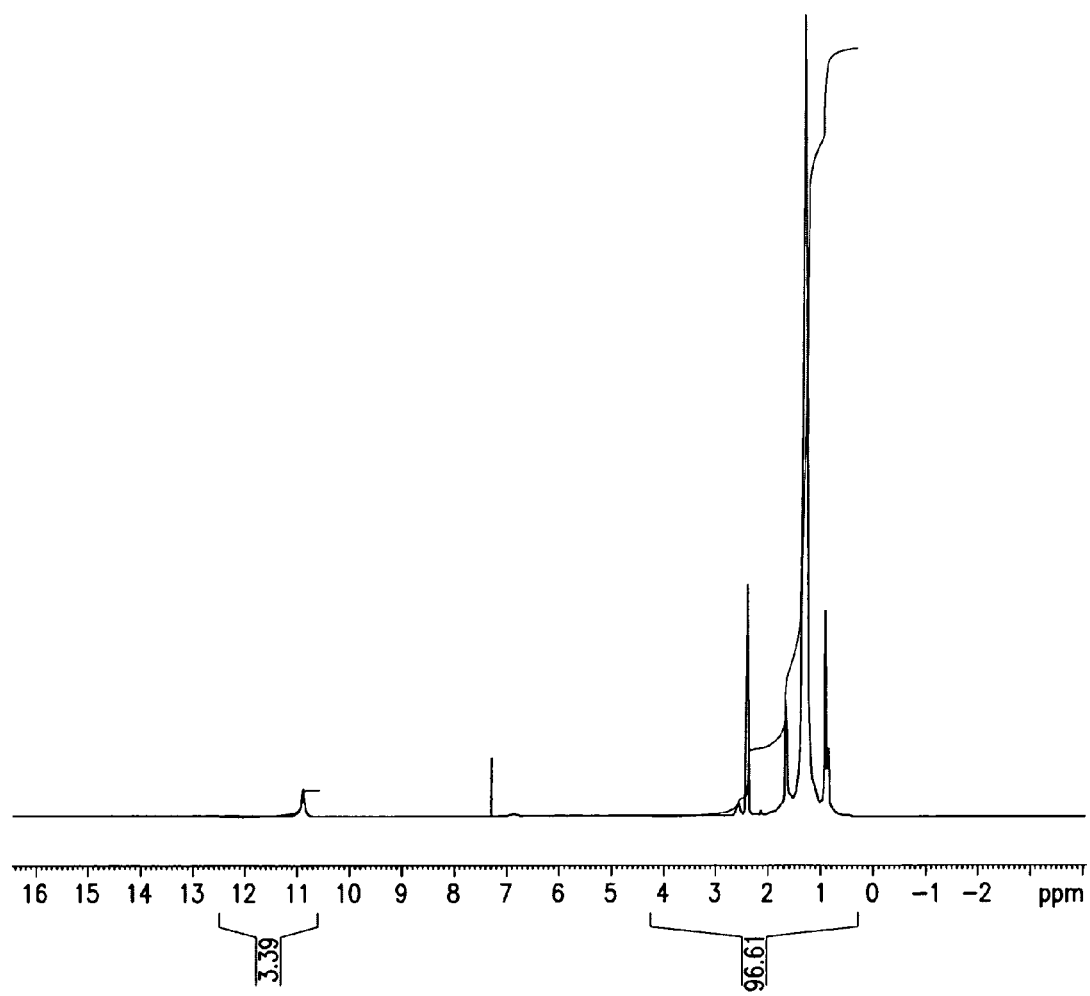
FIG. 1 is the 1H NMR spectrum of hydrogenated dimer acid that was used as the starting material for Examples 1 and 2.
Figure 2:
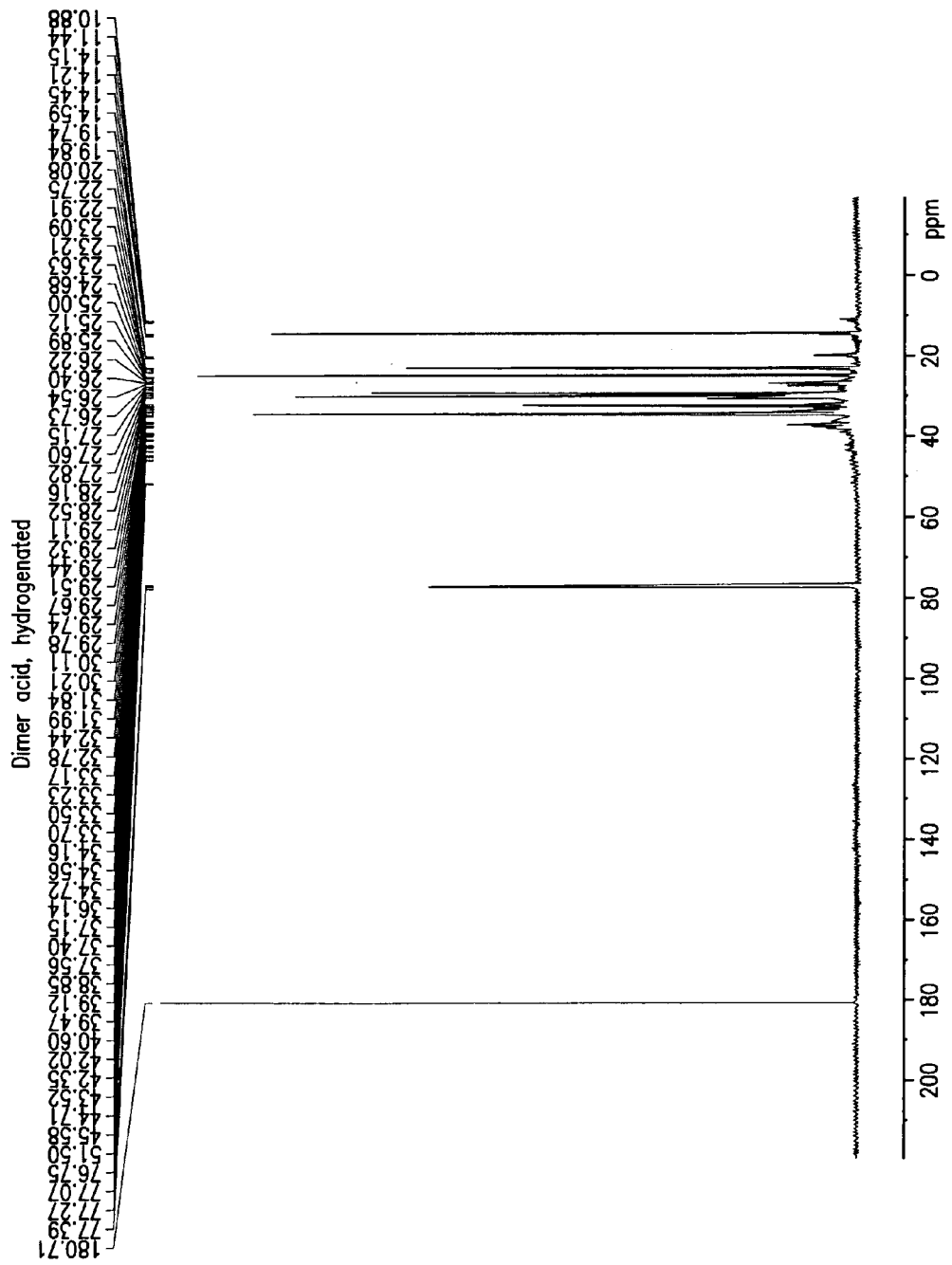
FIG. 2 is the $^{13}C$ NMR spectrum of hydrogenated dimer acid that was used as the starting material for Examples 1 and 2.
Figure 3:
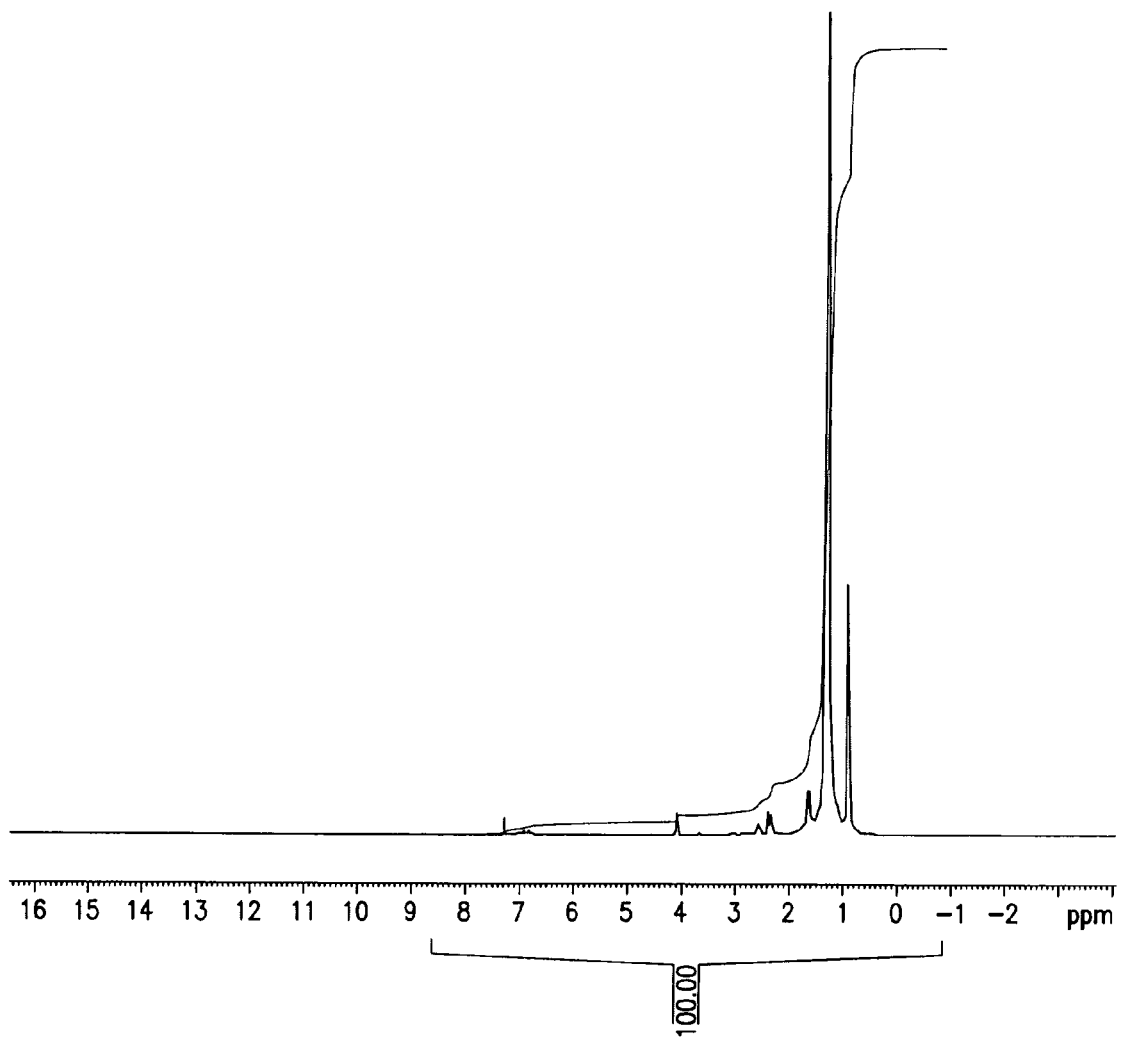
FIG. 3 is the $^1H$ NMR spectrum of products from Example 1.
Figure 4:
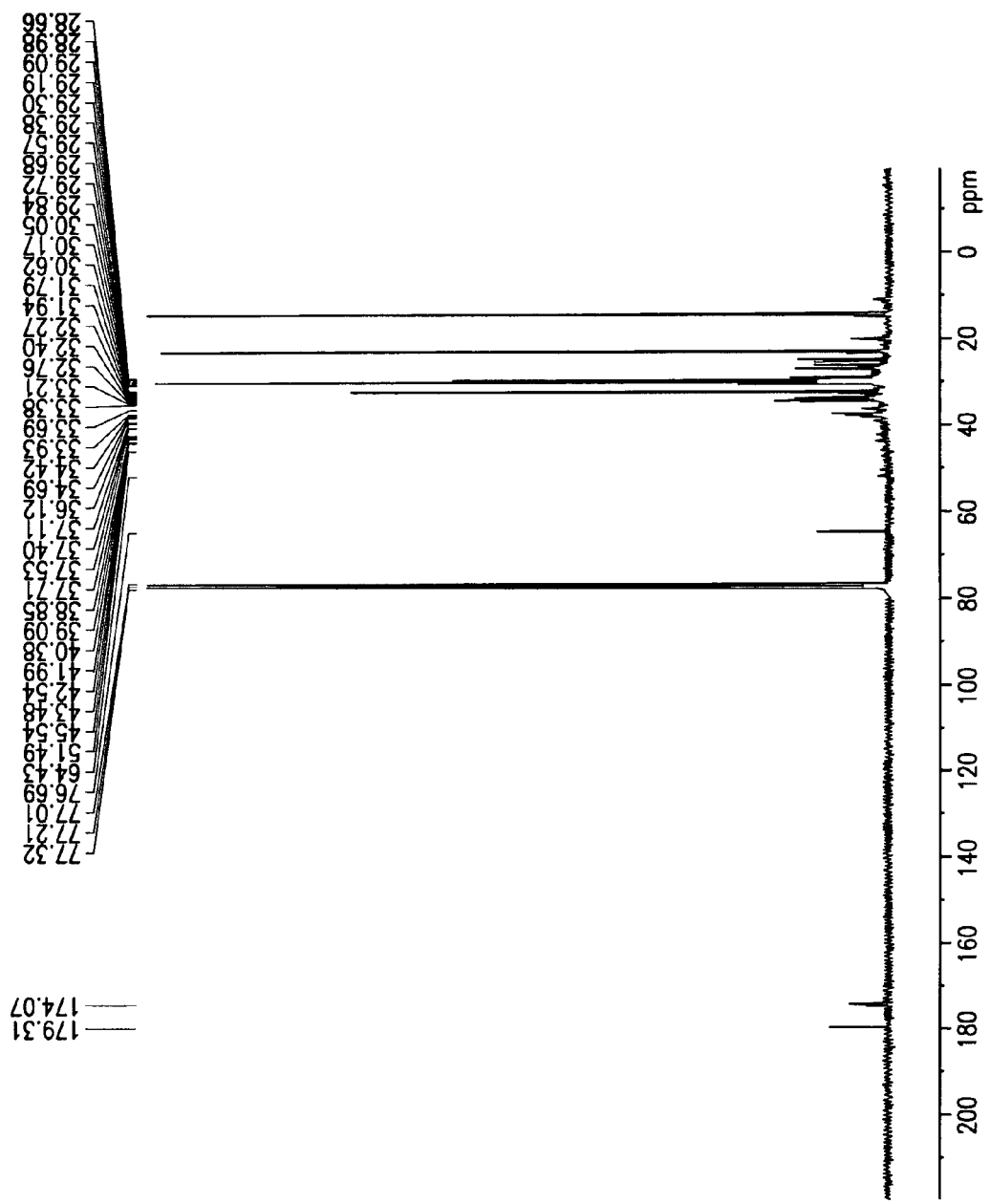
FIG. 4 is the $^{13}C$ NMR spectrum of products from Example 1.

All numerical values in this disclosure are understood as being modified by "about" or "approximately" the indicated value, and take into account experimental error and variations that would be expected by a person having ordinary skill in the art.

The present disclosure provides a process for making lube base oils of excellent quality from renewable biological sources. Fatty acids derived from natural oils from plant or animal or algae sources can be dimerized to form dimer acids. Subsequently, the C═C double bonds in the dimer acids are saturated and the oxygen removed in the form of $CO_2$, CO, or $H_2O$ under hydrogen atmosphere in a substantially single step. The resulting saturated hydrocarbon molecules have excellent lubricating properties approaching that of Group IV base oils.

In the process of the present disclosure, the feed comprises one or more component(s) selected from the group consisting of triglycerides, carboxylic acids having carbon numbers from $C_4$ to $C_{38}$, esters of $C_4$ to $C_{38}$ carboxylic acids and $C_1$-$C_{11}$ alcohols, $C_4$-$C_{38}$ carboxylic acid anhydrides, and $C_4$-$C_{38}$ alcohols. The feedstock is preferably selected from the group consisting of triglycerides, fatty acids having carbon numbers from $C_4$ to $C_{24}$, esters of $C_{12}$ to $C_{24}$ fatty acids and $C_1$-$C_3$ alcohols, $C_{12}$-$C_{24}$ fatty acid anhydrides, and $C_{12}$-$C_{24}$ fatty alcohols, and mixtures thereof. The feedstock preferably originates from starting materials of biological origin, or mixtures thereof.

Suitable starting materials of biological origin are selected from the group consisting of: a) plant fats, plant oils, plant waxes; animal fats, animal oils, animal waxes; fish fats, fish oils, fish waxes, and mixtures thereof; and b) free fatty acids or fatty acids obtained by hydrolysis, acid transesterification or pyrolysis reactions from plant fats, plant oils, plant waxes, animal fats, animal oils, animal waxes, fish fats, fish oils, fish waxes, and mixtures thereof; and c) esters obtained by transesterification from plant fats, plant oils, plant waxes, animal fats, animal oils, animal waxes, fish fats, fish oils, fish waxes, and mixtures thereof, and d) esters obtained by esterification of free fatty acids of plant, animal and fish origin with alcohols, and mixtures thereof; and e) fatty alcohols obtained as reduction products of fatty acids from plant fats, plant oils, plant waxes, animal fats, animal oils, animal waxes, fish fats, fish oils, fish waxes, and mixtures thereof; and f) waste and recycled food grade fats and oils, and fats, oils and waxes obtained by genetic engineering, and mixtures thereof; and g) mixtures of said starting materials.

In this context, plants and animals also include algae and insects, respectively. The starting material of biological origin may also contain free carboxylic acids and/or esters of carboxylic acids, or oligomerization products of biological starting materials, without substantially interfering with the process. Suitable feed-stocks are also all compound types mentioned that are produced either totally or partly synthetically.

Advantageous starting natural oils for the processes of the present disclosure should contain a relatively high amount of components having a single double bond in the fatty acid (e.g., mono-unsaturated fatty acids). Examples of the mono-unsaturated fatty acids include cis-5-dodecenoic acid, myristoleic acid (cis-9-tetradecenoic acid, C14:1), palmitoleic acid (cis-9-hexadecenoic, C16:1), oleic acid (cis-9-octadecenoic acid, C18:1), gadoleic acid (cis-11-eicosenoic acid C20:1), erucic acid (cis-13-docosenoic acid C22:1). Although most natural occurring oils contain cis-isomers of fatty acids, their trans-analogs occurred naturally or via isomerization process during treatment, such as hydrogenation, can also be used. Other odd carbon number mono-unsaturated acids, cis or trans form, although rare in natural products, can also be used. Generally, oils rich in the cis-form of the mono-unsaturated acids are most abundant in natural oils especially plant-based oils, and are the preferred feeds. For example, Canola oil, some rapeseed oil or some mustard oil contains 57%-60% monounsaturated fat, olive oil is has 75% monounsaturated fat while tea seed oil commonly contains over 80% monounsaturated fat. Oils that contain some di-unsaturated fatty acid moiety can also be used for the processes disclosed herein. For lube applications, it may be advantageous to use oils with low amount of di-unsaturated fatty acid moiety.

When choosing a feed from animal fats, it is advantageous to choose one that contains high percentages of mono-unsaturated fatty acids and low amounts of fully saturated fatty acid or multi-unsaturated fatty acid. Although animal fats, lard and oils can be used for this process, the yields to unsaturated fatty acids and the final synthetic hydrocarbon base stocks may be lower than from plant-based oils because most animal fats, such as beef fat, pork fat, and suet, contain higher amounts of saturated fats than plant-based oils.

Freshly produced plant-based oils or animal-based fats/oils can be used as starting material. Used or treated plant oil or animal fats/oils can also be used as starting material. The used plant oils can be obtained from food preparation, cooking, or other processes that recover or recycle used plant oils or animal fats/oils. Many of the used plant oils may contain partially hydrogenated plant oils. Thus, they may contain glycerides of the naturally occurring acids (mostly cis-acids) and also glycerides of the corresponding isomerized trans-acids. These trans-acids of mono- or di-unsaturated acids are also suitable for the processes of this disclosure. In order to optimize product yields, the impurities in the used plant oils, such as water, decomposed products, sludge, and carry-over component from the foods should be removed by pretreatments known in the art, such as settlement and decantation, clarification, passing through drying column and similar procedures.

The rapeseed oils, canola oils, mustard oils or olive oils usually are triglycerides of long-chain fatty acid esters. In particular, suitable seed oils for this embodiment may include oils which have a significant amount of the glycerides of mono-unsaturated acids, such as myristoleic acid, palmitoleic, oleic, gadoleic, behenic, erucic, and lauroleic acids. These fatty acids are most suitable in this disclosure. Fatty acid compositions of common plant oils are listed in Table 2.

Soybean oil contains a relatively high amount of di-unsaturation in the form of linolenic acid in the fatty acid moiety. It can be used as a starting material for this process. However, the high content of di- or tri-unsaturated fatty acids is not as desirable as the mono-unsaturated acids or esters. There are many reports of utilizing a genetically modified soybean plant to produce soybean oil ["Genetic enhancement of soybean oil for industrial uses: prospects and challenges", by Edgar B. Cahoon, USDA Research Service, AgBioForum 6 (1&2): 11-13; at the 2003 AgBioForum, and references therein]. Such genetically modified soy beans can produce oil with very high amount of oleic acid moiety, sometimes as high as 85% oleic acid content, vs. 25% oleic acid content from the traditional, i.e., naturally occurring, soybean plant. Oils from these genetically modified soybean plant with high oleic content are most-suitable for the processes described herein.

TABLE 2

Compositions of Common Plant Oils

| (Cn:no. of double bonds) | Soybean Oil (wt %) | Canola Oil (wt %) | Rapeseed Oil (wt %) | Sunflower Oil (wt %) | H. Mustard 2 (wt %) |
|---|---|---|---|---|---|
| Myristic (14:0) | | | | 0.1 | |
| Palmitic (16:0) | 11.0 | 3.9 | 2.8 | 6.1 | 2.5 |
| Palmitoleic (16:1) | 0.1 | 0.2 | 0.2 | | |
| Stearic (18:0) | 4.0 | 1.9 | 1.3 | 5.3 | 2.4 |
| Oleic (18:1) | 23.4 | 64.1 | 23.8 | 21.4 | 56.3 |
| Linoleic (18:2) | 53.2 | 18.7 | 14.6 | 66.4 | 5.5 |
| Linolenic (18:3) | 7.8 | 9.2 | 7.3 | | 2.2 |
| Arachidic (20:0) | 0.3 | 0.6 | 0.7 | | |
| Gadoleic (20:1) | | 1.0 | 12.1 | | 4.5 |
| Eicosadienoic (20:2) | | | 0.6 | | |
| Behenic (22:0) | 0.1 | 0.2 | 0.4 | | |
| Erucic (22:1) | | | 34.8 | | 20.7 |
| Others | | 0.2 | 1.3 | | |

In addition to the plant oils or animal fats/oils that can be used for these processes, the fatty acid derivatives from plant oils or animal fats/oils can also be used herein. Examples of the derivatives include mono-esters derived from triglycerides (also known as mono-esters of the fatty acid moieties of the triglycerides). Methods of making such derivatives are known in the art, e.g., see Process Economic Program Report 251 "Biodiesel Production" by Stanford Research Institute (SRI), or U.S. Pat. Nos. 4,303,590; 5,354,878; and 5,525,126 and U.S. Patent Application Publication Nos. 2002/0010359 and 2003/0149289. Further examples of such derivatives include methyl esters of these fatty acids, commonly known as fatty acid methyl ester (FAME) or biodiesel, ethyl esters, propyl esters, and simple fatty acids. In the cases of the derivatives such as the methyl ester or unsaturated fatty acids, they can also be oligomerized to give oligomeric esters which can be converted into saturated hydrocarbons.

Since the purpose of the first step in the process is the oligomerization of components having double bonds, the feedstock preferably contains at least 10%, and more preferably at least 50%, by weight, of unsaturated and/or polyunsaturated compounds. The unsaturated compound can be mono- or poly-unsaturated, but is preferably a mono-unsaturated component, particularly preferably a $C_{16}$:1 and/or $C_{18}$:1 component present in the feedstock in concentrations of above 10%, and preferably above 40%, by weight.

Unsaturated fatty acids can be obtained from triglycerides in natural oil via hydrolysis. In a hydrolysis treatment, oils and fats react with water yielding free fatty acids and glycerol as the product. Three main processes for the industrial production of fatty acids are known: vapor splitting of triglycerides under high pressure, basic hydrolysis, and enzymatic hydrolysis. In the vapor splitting process, the hydrolysis of triglycerides using steam is carried out at temperatures between 100 and 300° C., under a pressure of 1-10 MPa, preferable conditions being from 250 to 260° C. and from 4 to 5.5 MPa. Metal oxides like zinc oxide may be added as the catalyst to accelerate the reaction.

In the processes of the present disclosure, especially oligomerization reactions of materials of biological origin may be utilized in combination with hydrogenation reaction for the production of saturated hydrocarbons in a novel manner. For the oligomerization of unsaturated carboxylic acids and/or derivatives thereof, such as fatty acids, fatty acid esters, fatty alcohols, fatty acid anhydrides, and/or mixtures thereof, the monomers are converted into dimers with two monomers and/or into higher oligomers with three or more monomer units. In cases where starting materials of biological origin are used for the production of base oils, it is necessary to extend the hydrocarbon chain length to reach the carbon number range required in the base oil applications, leaving predominantly carbon-carbon bonds in the main structure of the molecule. According to the disclosure, this is carried out by allowing the compounds having double bonds to react with each other, thus yielding hydrocarbons with carbon numbers in the range from $C_{18}$ to $C_{180}$. In base oil applications, the carbon number range is typically from $C_{18}$ to $C_{144}$. In the oligomerization reaction, for instance, double bonds of the unsaturated fatty acid molecules react with each other, thus forming oligomers of fatty acids. For lube base oil applications, dimers of unsaturated fatty acids are the most preferable form, although trimers and tetramers are also formed and may be used. In case the feedstock contains polyunsaturated hydrocarbon chains, after oligomerization and hydrogenation treatment, greater amounts of trimers and hydrocarbons with ring structures are obtained than with monounsaturated hydrocarbon chains. Generally, it is preferable to use feed stock containing higher than 20% mono-unsaturated acid or ester, alternatively, higher than 40%, alternatively, higher than 50%, alternatively higher than 60% or alternatively high than 70%, alternatively higher than 80%, or alternatively greater than 90% mono-unsaturated acid or ester. Mixed unsaturated acid or esters, containing $C_{12}$, $C_{14}$, $C_{16}$, $C_{18}$, $C_{20}$, $C_{22}$, or $C_{24}$ unsaturated acid and/or esters can be used as feed. It is also preferable to choose the combination of the acids to give the average carbon number of feeds in the range of $C_{14}$ to $C_{22}$. This range of feed will most likely produce final lube base stock with viscosity similar to Group IV base stock, ranging from 3 cSt at 100° C. to 100 cSt at 100° C. Unsaturated fatty acids can be used as starting materials. Corresponding unsaturated fatty esters mixtures of fatty acid and esters can also be used as starting materials to give the same final product.

The unsaturated fatty acids obtained from hydrolysis of natural oils are oligomerized to form dimers and/or higher oligomers of unsaturated fatty acids. Oligomerization reactions are carried out with suitable catalysts at high temperature. Suitable catalysts include molecular sieves (both aluminosilicate zeolites and silicoaluminophosphates), amorphous aluminosilicates, cationic acidic clays, and other solid acid catalysts. According to International Zeolite Association (IZA) definitions, molecular sieves can be categorized according to the size of the pore opening. Examples of the molecular sieves can be of the large (>12-ring pore opening), medium (10-ring opening) or small (<8-ring pore opening) pore type. The molecular sieves structure types can be defined using three letter codes. Non-limiting examples of small pore molecular sieves include AEI, AFT, ANA, APC, ATN, ATT, ATV, AWW, BIK, CAS, CHA, CHI, DAC, DDR, EDI, ERI, GIS, GOO, KFI, LEV, LOV, LTA, MER, MON, PAU, PHI, RHO, ROG, SOD, THO, and substituted forms thereof. Non-limiting examples of medium pore molecular sieves include AFO, AEL, EUO, HEU, FER, MEL, MFI, MTW, MTT, MWW, TON, and substituted forms thereof. Non-limiting examples of large pore molecular sieves include BEA, CFI, CLO, DNO, EMT, FAU, LTL, MOR and substituted forms thereof. More preferred zeolite catalyst have a Si/Al molar ratio of greater than 2 and at least one dimension of the pore openings greater than or equal to 10-ring. Most preferred solid zeolites include ZSM-5 (MFI), zeolite beta (BEA), USY family zeolites (FAU), MCM-22, MCM-49, MCM-56 (MWW). Mesoporous materials with pore openings greater than 20 Å, such as the MCM-41 family and SBA-15 type with aluminum incorporated into the structure and thus possess acidity, can also be used as oligomerization catalysts. Acidic clays include acidic, natural or synthetic Montmorillonites, bentonite, silica clay, alumina clay or magnesia clay or silica-alumina clay. Commercially available acidic forms of Filtrol clays are also suitable for this oligomerization process. Other solid acid catalysts, such as activated $WOx/ZrO_2$ catalysts, other metal oxides, Nafions or other acidic ion-exchanged resins, such as Dowex or Amberlyst cation exchanged are also suitable for the oligomerization reaction.

These oligomerization reactions can be carried out at 50° C. to 350° C., preferably 100° C. to 250° C., preferably 100° C. to 200° C. The reaction pressure can be atmospheric pressure to 500 psi. Atmospheric pressure or slightly above, up to 150 psi are convenient operating pressure. The reaction can also be carried out in the presence of small amount of hydrogen gas to prevent or improve catalyst aging and promote long catalyst lifetime. The hydrogen pressure can range from 1 psi to 300 psi, alternatively, 5 psi to 250 psi, alternatively 30 psi to 200 psi, and alternatively 50 to 250 psi. Optimum amount of hydrogen is used to reduce coke or deposit formation on catalyst, to promote long catalyst life time without significant hydrogenation of mono-unsaturated fatty acids. Furthermore, the presence of hydrogen may slightly reduce the di- or poly-unsaturated fatty acid. Thus, the presence of hydrogen may reduce the cyclic dimer or oligomer formation. This is beneficial for production of high paraffinic hydrocarbons at the end of the conversion. When solid catalyst is used, the reaction can be carried out in batch mode or in continuously stirred tank (CSTR) mode, or in fixed bed continuous mode. In a batch or CSTR mode, the amount of catalyst used may vary from less than 0.01% to 30 wt % of the feed, preferably 0.5 to 10 wt %, depending on reaction time or conversion level. The reaction time or residence time may vary from 5 minutes to 50 hours, preferably 20 minutes to 10 hours, preferably 30 minutes to 5 hours. The crude product can be isolated by filtration to remove the product. In fixed bed mode, the reaction residence time may vary from 5 minutes to 50 hours, preferably 20 minutes to 10 hours, more preferably 30 minutes to 5 hours; the weight hourly space velocity may vary from 0.2 g of feed/g of catalyst to 50 g of feed/g of catalyst, and preferably 0.3 to 10 g of feed/g of catalyst. The final conversion level varies from 10% to 100%, and alternatively from 20% to 90%. Usually high conversion is better. High conversion minimizes problems associated with product separation. In some instances, partial conversion, such as 50 to 80%, is preferred to prevent excessive formation of undesirable by-products.

The oligomerization reaction can also be catalyzed by homogeneous catalysts. Examples are hydrochloric acid, sulfuric acid, nitric acid, other small carboxylic acids or $BF_3$, promoted $BF_3$ catalysts, $AlCl_3$ or promoted $AlCl_3$ catalysts. When these homogeneous catalysts are used, 0.1 wt % to 10 wt % of catalyst may be used. Reaction temperatures for homogeneous acid catalyzed reaction range from 20° C. to 150° C. At the end of the reaction, these homogeneous acid catalysts are removed by aqueous wash or by adsorption by solid sorbents. The oligomerization reaction can also be catalyzed by the fatty acid itself when no other catalysts are added.

Generally, certain type of catalysts, such as shape-selective zeolites, the MCM-22 family (MWW), or the USY family (FAU), may impart unique control of the oligomerization reaction to favor the formation of dimer acid and minimize the formation of higher oligomers. The oligomerization by homogeneous catalysts, amorphous catalysts or clays may promote oligomerization to give higher degrees of oligomerization, such as trimers and tetramers. Furthermore, the proper choice of catalyst, catalyst pretreatment conditions, reaction temperature, and reaction time should help to minimize formation of cyclic dimer acid or ester, or hydrogen transfer reaction to produce poly-unsaturated starting acid or dimer acid and co-production of saturated starting acid. Formation of saturated starting acid will decrease the ultimate lube yields. Many clays, especially natural montmorillonite clay, can catalyze dimer formation with significantly higher amount of cyclic dimer formation. Molecular sieve catalysts can provide advantages of more dimerization and less cyclization. This improves the non-naphthene or paraffinic content of the finished lube base oil product.

The choice of catalyst is important for high conversion. Use of low cyclic oligomers and/or low hydrogen transfer yields saturated acid/esters, and, ultimately, high yields of final lubes with high desirable paraffinic content. Generally, molecular sieve material and clays of high silica to alumina ratio ($SiO_2/Al_2O_3$) are more desirable. The ratio of silica to alumina of these materials can range from 1 to 10,000. Typically, it is preferable to have a ratio of silica to alumina of from 2 to 5000, alternatively from 2 to 1000, alternatively from 2 to 500, alternatively from 4 to 1000, alternatively from 4 to 500, alternatively from 4 to 300, alternatively from 10 to 1000, or alternatively from 10 to 200. Higher silica to alumina ratio is generally equivalent to lower total number of acid sites. A lower total number of acid sites usually promotes the dimerization or oligomerization reaction and reduces the hydrogen transfer reaction, which reduces the formation of coke or very high molecular weight carbonaceous material, which prolongs catalyst lifetime and increase catalyst productivity.

Synthetic microporous materials are generally more preferable than naturally occurring clay materials because synthetic materials typically have a more controlled silica to alumina ratio and more controlled acid site density. Naturally occurring clay materials usually have very high density of acid sites, which promotes by-product formation and reduces catalyst productivity. Also, many naturally occurring clay materials have high amounts of other metal components, such as iron, calcium, and magnesium. These metals or oxides thereof promote by-product formation and reduce catalyst productivity.

In the processes of the current disclosure, the oligomerization products of unsaturated fatty acids or esters have less than 90% by weight of cyclic oligomers, preferably less than 80% by weight of cyclic oligomers, preferably less than 70% by weight of cyclic oligomers, preferably less than 60% by weight of cyclic oligomers, preferably less than 50% by weight of cyclic oligomers, preferably less than 40% by weight of cyclic oligomers, preferably less than 30% by weight of cyclic oligomers, preferably less than 20% by weight of cyclic oligomers, and still more preferably less than 10% by weight of cyclic oligomers. The products of the present disclosure may also have less than 3.0% by weight of cyclic oligomers, preferably less than 1.0% by weight of cyclic oligomers, and most preferably less than 0.1% by weight of cyclic oligomers.

The C═C double bond(s) in dimer acids can be saturated and the oxygen atoms removed in the form of $CO_2$ or CO or $H_2O$ in a single hydrogenation step. As used herein, the term "hydrogenation" is used to describe these conversions without specifically implying the actual reaction mechanisms or pathways. Alternatively, the term "hydro-deoxygenation" can be used to describe the conversion where the oxygen is substantially removed in the form of $H_2O$ and the double bonds are substantially saturated by hydrogen. Alternatively, the term "hydro-decarbonylation" can be used to describe the conversion where the oxygen is substantially removed in the form of CO and the double bonds are substantially saturated by hydrogen. Alternatively, the term "hydro-decarboxylation" can be used to describe the conversion where the oxygen is substantially removed in the form of $CO_2$ and the double bonds are substantially saturated by hydrogen.

In one embodiment of this disclosure, the acid functionalities, i.e., carboxylic acid groups, are substantially removed in the form of $CO_2$ and double bonds are substantially saturated by hydrogen, in a single operation step. Consequently the term "hydro-decarboxylation" is used to describe the conversion. Removal of double bonds is inclusive of both aliphatic double bonds and aromatic double bonds. Hydro-decarboxylation can be carried out in a batch reactor such as an autoclave. The autoclave can have either static $H_2$ gas supply or flow-through capability of $H_2$ gas. Hydrogen pressure should be greater than atmospheric, preferably greater than 1 MPa, more preferably higher than 3 MPa. Temperature for the reaction should be in the range from 100 to 500° C., preferably from 200 to 400° C., and more preferably from 250 to 350° C. Catalysts suitable for the conversion reaction include metals such as Mo, Re, Fe, Ru, Co, Rh, Ir, Ni, Pd, Pt, Cu, Zn, as well as binary or ternary mixtures thereof supported on silica, alumina, zirconia, clays such as Kieselguhr, amorphous aluminosilicates, or zeolites. More preferably, the catalysts include Mo, Co, Ni, Pd, Pt, and binary or ternary mixtures thereof supported on silica, alumina, amorphous aluminosilicates, or clays, especially Kieselguhr. Most preferably the catalysts are Ni supported on Kieselguhr, CoMo/γ-$Al_2O_3$, and NiMo/γ-$Al_2O_3$. Metal content in the catalyst ranges from 0.1 wt % to 70 wt % of the catalyst. Loading of the catalyst is 1-30% by weight of the dimer acids, preferably 2-20%, or more preferably 5-10% by weight. Duration of the reaction ranges from 1-48 hours, or 1-20 hours, or 12-36 hours, or 24-30 hours. This conversion step can be carried out in fixed bed reactor, continuous stir tank reactor, or batch reactor. In any of these operations, it is advantageous to maintain partial pressure of hydrogen above 300 psi, or above 400 psi, or above 500 psi, or above 600 psi, or above 700 psi. During conversion, if $CO_2$, CO or $H_2O$ are generated, they can be present as gaseous form, thus increasing the total reactor pressure. Under this condition, it is important to maintain hydrogen partial pressure. This can be achieved by intermittently purge of the reactor gas, re-charge with hydrogen gas in batch or CSTR operation. Or alternatively, as in fixed bed operation, this can be achieved by withdrawing reactor gas at different location along the in fixed bed reactor; by two-stage hydrogenation with drawing reactor gas in between stages, or alternatively by stage injection of hydrogen. Many other means to maintain hydrogen pressure is also possible.

The reaction time or residence time can range from 5 minutes to 50 hours depending on type of catalyst used, reaction temperature and the amount (wt %) of catalyst in reactor. It is preferred to have a residence time of 10 minutes to 10 hours. Shorter residence time gives better efficiency for reactor usage. Longer residence time ensures high conversion to pure hydrocarbons. Usually an optimized reactor time is most desirable.

In various process steps disclosed herein, hydrocarbons may be used as diluents in the feedstock. Hydrocarbon can be for instance from biological origin and boil in diesel fuel range between 150 and 400° C., typically between 180 and 360° C. Sometimes, non-biological originated solvent can also be used. This includes solvents derived from petroleum or coal.

The carbon number and the carbon number range of the base oil depend both on the biological starting material of the feedstock and the production process. A conventional carbon number range of the base oil applications is from $C_{18}$ to $C_{76}$, whereas the carbon number range of particularly thick base oils may be as high as from $C_{150}$ to $C_{550}$.

Selection of the biological feedstock has a strong influence on the composition and boiling range of the product. Moreover, the feed may be fractioned by distillation to fractions having narrow carbon numbers that may be tailored for different applications. For feed-stocks containing carbon number $C_n$, where n=12, 14, 16, 18, 20, 22, or 24, the final hydrocarbon products may contain the carbon number of $x*C_n$, $x*C_n-1$, $x*C_n-2$, and down to $x*C_n-x$ (* is the multiplication sign), where x is the degree of oligomerization and can be any integer in the range of 2-10, preferable be 2-5, more preferably 2-3, and most preferably 2. For feed-stocks containing mixtures of unsaturated fatty acids with carbon numbers $C_n$ and $C_m$, where n and m can be 12, 14, 16, 18, 20, 22, or 24, dimerization will lead to products with carbon number of $C_{2n}$, $C_{n+m}$, and $C_{2m}$. Subsequent hydrogenation treatment will give hydrocarbon products containing carbon numbers of $C_{2n}$, $C_{2n-1}$, $C_{2n-2}$, $C_{n+m}$, $C_{n+m-1}$, $C_{n+m-2}$, $C_{2m}$, $C_{2m-1}$, and $C_{2m-2}$.

In one embodiment of the current disclosure, feed-stocks having hydrocarbon chain lengths of $C_{16}$, $C_{18}$, $C_{20}$, and $C_{22}$ and mixtures thereof can be used, dimerization gives dimer acids with the carbon number range of $C_{32}$-$C_{44}$. Hydrogenation treatment of the dimer acids gives carbon numbers of the hydrocarbon products in the range of $C_3$-$C_{44}$. The low end carbon number $C_{30}$ is achieved by hydro-decarboxylation of the $C_{32}$ dimer acids, while the high end carbon number $C_{44}$ is achieved by hydro-deoxygenation of $C_{44}$ dimer acids. Since the distillation range of the product mainly depends on the hydrocarbon chain length, narrow product fractions are obtained.

The carbon number range of the base oil or base oil component produced by the oligomerization and hydrogenation or hydro-decarboxylation process of the disclosure is narrow. For example, starting from feed-stocks containing $C_{18}$ unsaturated fatty acids, the carbon numbers in the products range from $C_{33}$ to $C_{36}$.

The molecular mass of the product may be adjusted according to carbon number ranges necessary for different applications by adding suitable unsaturated carboxylic acids or olefins to the feedstock. Carboxylic acids having small molecules, or olefins cross-linking or oligomerizing with the fatty acids of triglycerides form short branches on the main hydrocarbon chain of the fatty acid. In case other natural cyclic compounds such as alpha pinene are used as additional components of the feedstock, molecules having ring structures in the side chain within the molecular chain are obtained. One or two additional components are preferably oligomerized in the product. According to the disclosure, corresponding products tailored with respect to hydrocarbon chain lengths may also be produced from other carboxylic acids and from other biological components with short chains.

The base oil of biological origin according to the disclosure comprises a mixture of saturated hydrocarbon products. Said products are produced from biological starting material, said products containing at least 70%, preferably at least 80%, particularly preferably at least 90%, and at still more preferably 99% by weight, of saturated hydrocarbons. Moreover, the products of the disclosure contain more than 5%, preferably more than 10%, preferably more than 20%, preferably more than 30%, preferably more than 40%, preferably more than 50%, preferably more than 60%, preferably more than 70%, preferably more than 75%, and particularly preferably more than 80%, particularly preferably more than 90%, particularly preferably more than 95%, of paraffinic hydrocarbons, based on the FIMS method. Alternatively, the products of this disclosure contains less than 90% mono-cyclic naphthenes, less than 80% mono-cyclic naphthenes, less than 70% mono-cyclic naphthenes, less than 60% mono-cyclic naphthenes, less than 50% mono-cyclic naphthenes, less than 40% mono-cyclic naphthenes, less than 30% mono-cyclic naphthenes, less than 20% mono-cyclic naphthenes, or less than 10% mono-cyclic naphthenes. The products of this disclosure contain less than 3.0%, preferably less than 1.0%, and particularly preferably less than 0.1% of polycyclic naphthenes by FIMS.

For base oils of the disclosure, the viscosity index is at least 100 and preferably at least 110, as determined by the method of ASTM D 2270. The viscosity index of the product may be as high as 120 or higher, the product thus being suitable in base oil applications of Group III.

Depending on the degree of oligomerization controlled by the selection of catalyst, reaction temperature, residence time, the base oil produced in this disclosure can have a 100° C. viscosity of 2.5 to 100 cSt, most preferably 2.5 to 10 cSt, or alternatively 3 to 10 cSt, or alternatively 3 to 20 cSt, or alternatively 3 to 50 cSt, or alternatively 4 to 10 cSt, or alternatively 4 to 20 cSt, or alternatively 4 to 8 cSt, or alternatively 15 to 100 cSt, or alternatively 20 to 80 cSt. For the low viscosity range product, the width or distribution of the carbon number range is no more than 10 carbons, preferably no more than 9 carbons, and particularly preferably no more than 4 carbons (determined by field ionization mass spectrometry, FIMS). More than 50%, preferably more than 75% and particularly preferably more than 80% by weight of the base oil contains hydrocarbons belonging to this narrow carbon number distribution.

Sulfur content of said base oil of the disclosure is less than 300 ppm, preferably less than 50 ppm, and particularly preferably less than 1 ppm (as measured by ASTM D 3120). Nitrogen content of said base oil of the disclosure is less than 100 ppm, preferably less than 10 ppm, and particularly preferably less than 1 ppm (as measured by ASTM D4629).

Volatility of the base oil with a narrow boiling range, obtained according to the disclosure and measured according to Noack Volatility method (or ASTM D5800 method), is extremely low compared to similar products of the prior art. The product Noack volatility can range from less than 5 wt % for a 20 cSt and higher viscosity product to less than 50 wt % for a fluid of 2.5 cSt. For a fluid of 3 to 8 cSt, the volatility typically can range from 3% to 25%. For fluid of 3.5 to 6 cSt, the volatility can range from 4% to 15% depending on fluid viscosity. For a 5.5 cSt base oil of this disclosure from a $C_{18}$ dimer acid, the Noack volatility is 5.5 wt %, lower than that of a higher viscosity PAO of 5.8 cSt with Noack Volatility of 6% to 9%, depending on source.

The base oil prepared according to the present disclosure is hydrolytically more stable and it has a structure not decomposing under humid conditions, unlike the esters and other base oils containing hetero-atoms, such as fatty alcohol dimers. In addition, the oxidation resistance of saturated hydrocarbons is better than that of corresponding base oils containing unsaturated groups on the basis of fatty acid or fatty alcohol dimers, or ester base oils. A saturated hydrocarbon component does not decompose as easily as esters that from corrosive acids. A non-polar and saturated hydrocarbon component is obtained using the process of the present disclosure by removing the oxygen of alcohols, esters, or carboxylic acids in the hydrogenation step as well as the heteroatoms of any impurities of the feedstock. Oligomerizing carboxylic acid derivatives yield a structure having branches formed by carbon-carbon bonds following hydrogenation treatment. In oligomerization of $C_{12}$:1-$C_{20}$:1 feed, lengths of the obtained branches are typically from $C_3$ to $C_{11}$. Such hydrocarbons have very low pour points favorable for base oil applications, and thus the product is liquid at very low temperatures, and further, it has a superior viscosity index. The produced saturated hydrocarbon product is a suitable component of base oils without any mixing limitations, and further, it is compatible with lubricant additives.

Pour point of the high quality base oil obtained with the process of the present disclosure is usually, much lower than conventional Group I to Group III base stock obtained from direct petroleum processing. Depending on viscosity, the new base oil will have pour point less than −15° C., preferably less than −20° C., preferably less than −30° C., preferably less than −40° C., and accordingly, the base oil is very suitable for demanding low temperature conditions.

The properties of the hydrocarbon components produced according to the disclosure, and described in the following examples are excellent, and moreover, carbon number ranges and distillation ranges are very narrow. The process of the disclosure provides saturated hydrocarbons having superior viscosity properties and excellent low temperature properties. The products are well suited as base oils without blending limitations, and further, the products are also compatible with lubricant additives. The saturated hydrocarbons of the present disclosure can optionally be blended with other lube base stocks to form lubricants. Useful co-base lube stocks include Group I-V oils and gas-to-liquid (GTL) oils.

Lubricants incorporating the saturated hydrocarbons may optionally include lube base oil additives, such as detergents, dispersants, antioxidants, anti-wear additives, pour point depressants, viscosity index modifiers, friction modifiers, defoaming agents, corrosion inhibitors, wetting agents, rust inhibitors, and the like. The additives are incorporated with the saturated hydrocarbons to make a finished lubricant that has desired viscosity and physical properties. Typical additives used in lubricant formulation can be found in the book "Lubricant Additives, Chemistry and Applications", Ed. L. R. Rudnick, Marcel Dekker, Inc. 270 Madison Ave. New York, N.J. 10016, 2003.

The saturated hydrocarbons can be employed in the present disclosure in a variety of lubricant-related end uses, such as a lubricant oil or grease for a device or apparatus requiring lubrication of moving and/or interacting mechanical parts, components, or surfaces. Useful apparatuses include engines and machines. The base oil in this disclosure is most suitable for use in the formulation of automotive crank case lubricants, automotive gear oils, transmission oils, many industrial lubricants including circulation lubricant, industrial gear lubricants, grease, compressor oil, pump oils, refrigeration lubricants, hydraulic lubricants, metal working fluids.

Furthermore, the base oils produced in this disclosure are derived from renewable sources; it is considered a sustainable product and can meet "sustainability" standards set by different industry groups or government regulations.

It was surprisingly found that with the process of the present disclosure comprising oligomerization and hydrodecarboxylation steps, high-quality hydrocarbon components and particularly saturated base oils may be produced from unsaturated carboxylic acids containing hetero-atoms, and from derivatives thereof, particularly from fatty acids, fatty acid esters, fatty alcohols, respective fatty acid anhydrides of biological origin, and/or mixtures thereof. The problems of the prior art processes and products obtained therewith may be avoided, or at least substantially reduced by means of the processes of the present disclosure.

The disclosure is now illustrated by means of the following non-limiting examples.

EXAMPLES

Example 1

Hydrogenation of Dimer Acid Using Supported Nickel Catalyst

An amount of 102.8 g hydrogenated dimer acid (CAS No. [68783-41-5], Aldrich catalogue #432369) was mixed with 5.32 grams of nickel on Kieselguhr (60 wt % nickel, Aldrich catalogue #208787) in a glass liner (catalyst loading: 5.2 wt %). The glass liner was then inserted in a 300-cc autoclave, sealed, and heated under a flowing $H_2$ (100 cc/min) at 516 psig and 300° C. with stirring for 24 hours. The products were separated by filtration and dried with anhydrous magnesium sulfate, yield 86% (24791-1234-4; theoretical yield: 89% for complete hydrogenation). Both NMR ($^1H$, $^{13}C$) and IR suggest that the carboxylic acid functionality has been significantly removed by hydrogenation (FIGS. 1-4, 6, and 7).

Example 2

Hydrogenation of Dimer Acid Using Supported Nickel Catalyst

Figure 5:
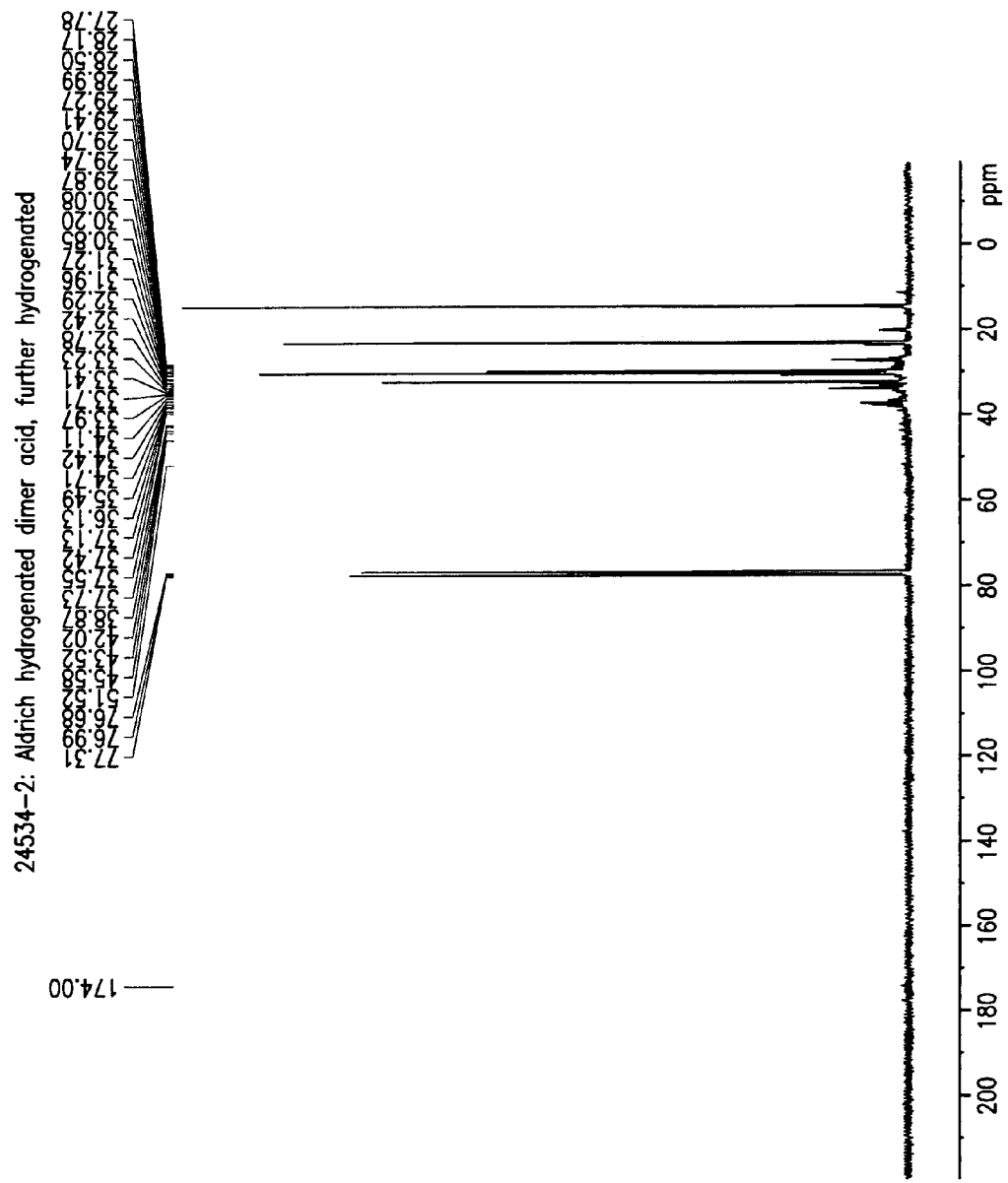
FIG. 5 is the $^{13}C$ NMR spectrum of products from Example 2.
Figure 6:
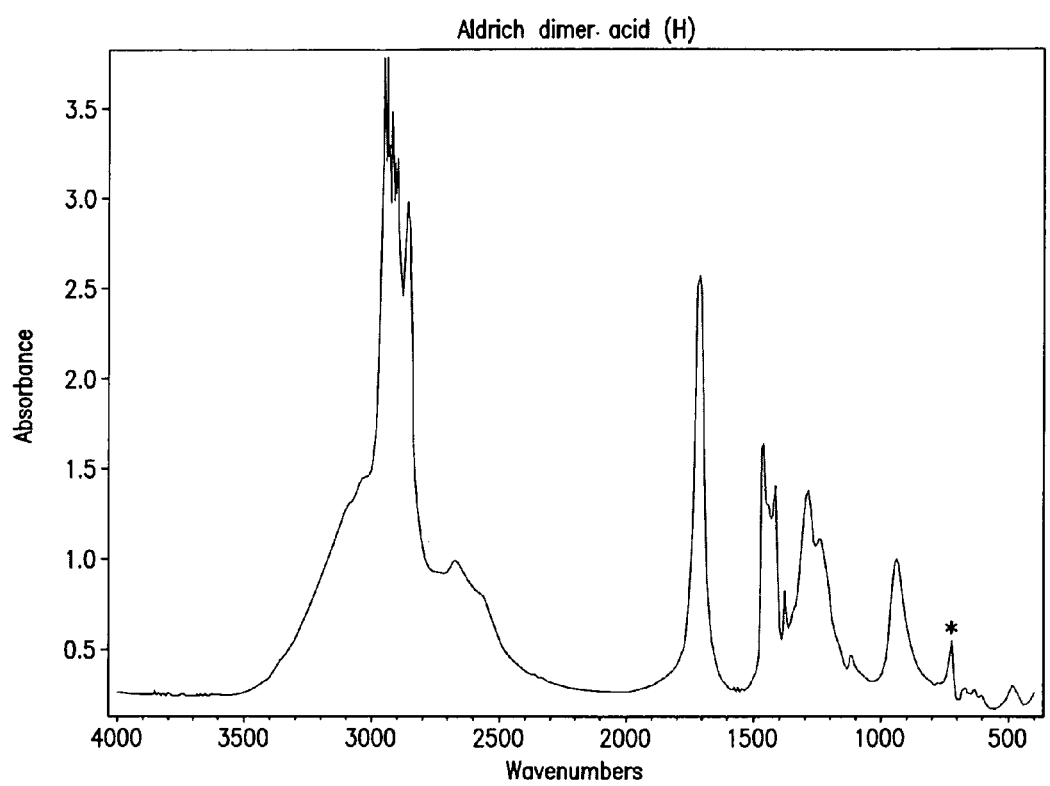
FIG. 6 is the IR spectrum of hydrogenated dimer acid that was used as starting material for Examples 1 and 2.
Figure 7:
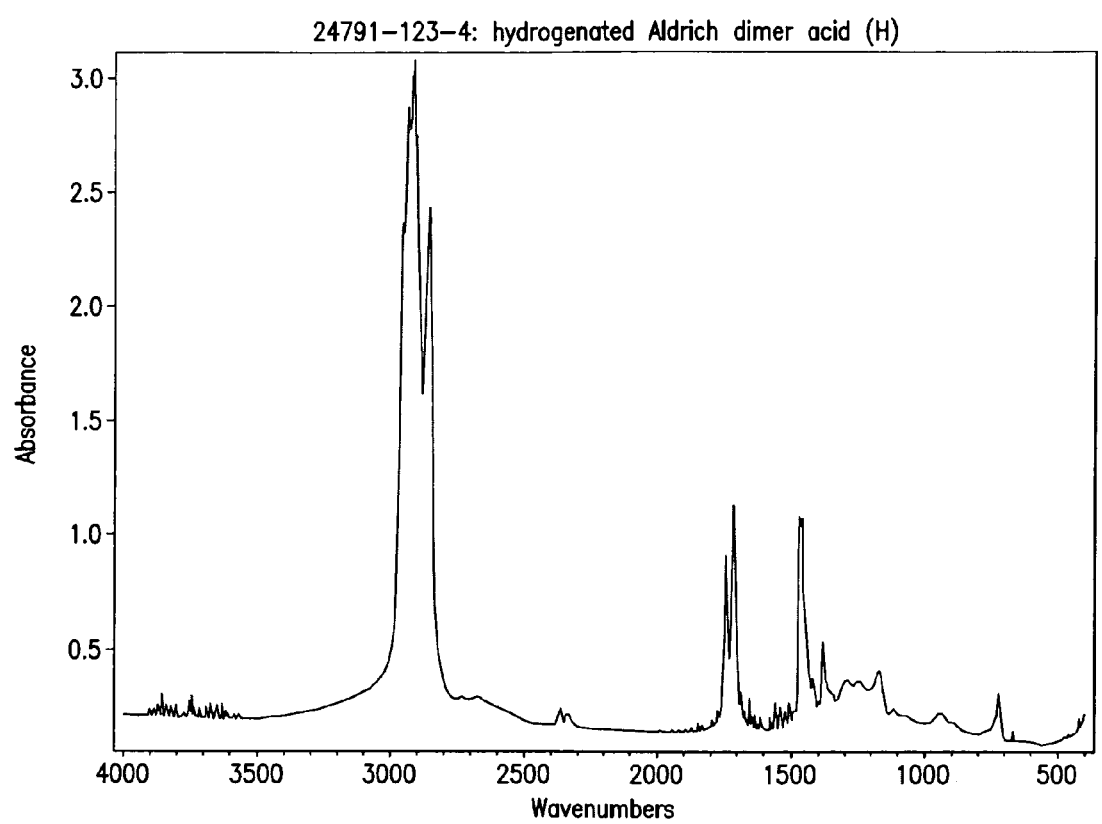
FIG. 7 is the IR spectrum of products from Example 1.
Figure 8:
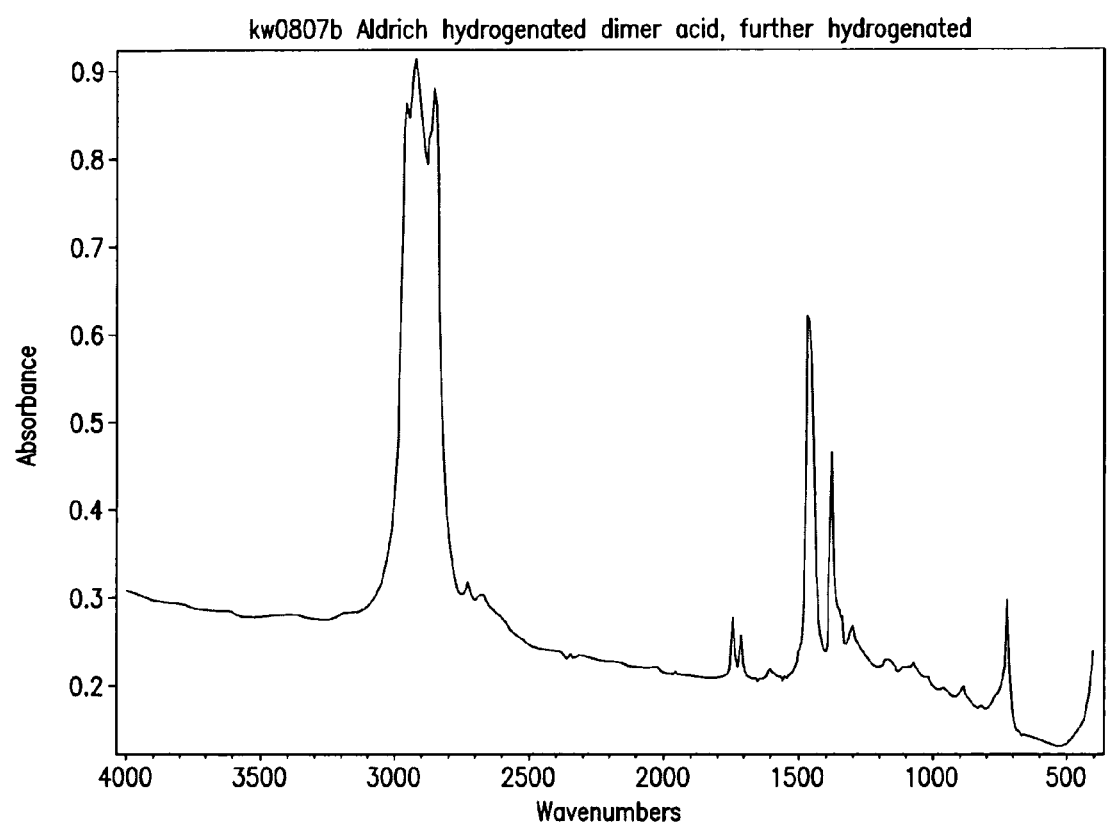
FIG. 8 is the IR spectrum of products from Example 2.

An amount of 110 grams hydrogenated dimer acid from Aldrich (CAS No. [68783-41-5], catalogue #432369) was mixed with 7.7 g of nickel on Kieselguhr (60 wt % nickel, Aldrich catalogue #208787) in a glass liner (catalyst loading: 7 wt %). The glass liner was then inserted in a 300-cc autoclave, sealed, and heated under a flowing $H_2$ (100 cc/min) at 520 psig and 313° C. with stirring for 24 hours. The products were separated by filtration and dried with anhydrous magnesium sulfate, yield 78% (24534-2; theoretical yield: 89% for complete hydrogenation). Both $^{13}C$ NMR and IR suggest that the carboxylic acid functionality has been nearly completely removed by hydrogenation (FIGS. 5 and 8).

Example 3

Hydrogenation of Dimer Acid Using Supported Nickel Catalyst

Figure 9:
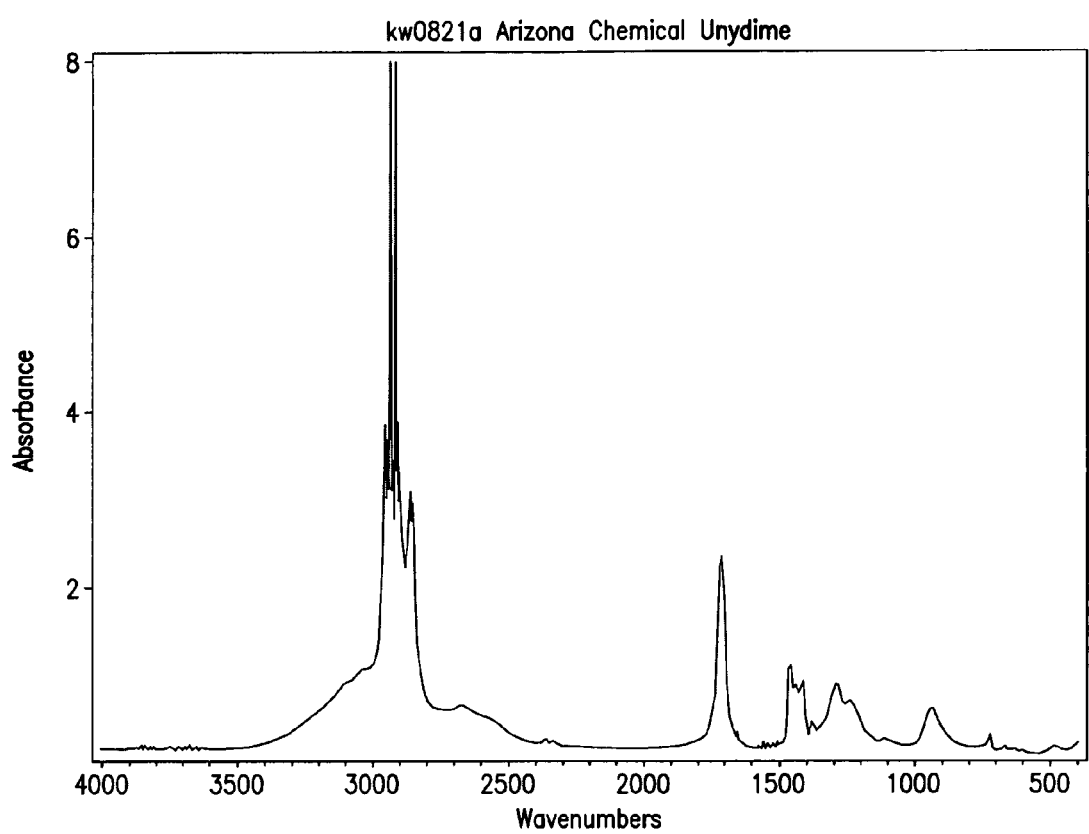
FIG. 9 is the IR spectrum of the starting material for Example 3.
Figure 10:
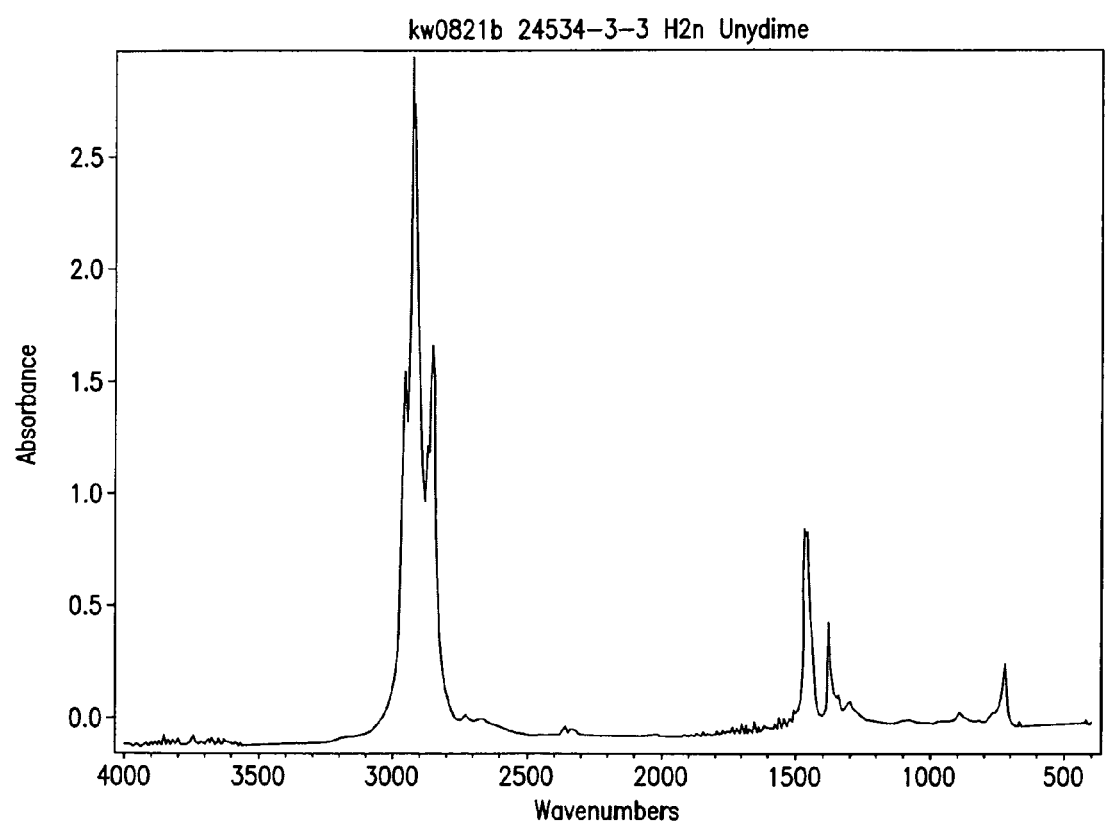
FIG. 10 is the IR spectrum of products from Example 3.

An amount of 150 grams dimer acid (UNIDYME from Arizona Chemical) was mixed with 10.5 grams of nickel on Kieselguhr (60 wt % nickel, Aldrich catalogue #208787) in a glass liner (catalyst loading: 7 wt %). The glass liner was then inserted in a 300-cc autoclave, sealed, and heated under a flowing $H_2$ at 100 cubic centimeters per minute (cc/min) at 516 pounds per square inch gauge (psig) and 310° C. with stirring for 26.75 hours. The products were separated by filtration, yield 77% (24534-3; theoretical yield: 89% for complete hydrogenation). IR suggests that the carboxylic acid functionality has been completely removed by hydrogenation (FIGS. 9-10).

Example 4

Physical Properties of Hydrogenated Products

Viscosity and pour point for the starting materials and their corresponding hydrogenated products were measured and the results are listed in the Table 3 below.

TABLE 3

|  | dimer acid - starting material for Examples 1 and 2 | Product from Example 1 | Product from Example 2 | UNIDYME- starting material for Example 3 | Product from Example 3 | PAO6 |
| --- | --- | --- | --- | --- | --- | --- |
| Hydrogenation catalyst |  | Nickel on Kieselguhr | Nickel on Kieselguhr |  | Nickel on Kieselguhr | From 1-decene |
| Wt % catalyst |  | 5.2 | 7 |  | 7 |  |
| Temperature (° C.) |  | 300 | 313 |  | 310 |  |
| $H_2$ pressure (psig) |  | 516 | 520 |  | 516 |  |
| $H_2$ flow rate (cc/minute) |  | 100 | 100 |  | 100 |  |
| Hydrogenation time (hours) |  | 24 | 24 |  | 26.75 |  |
| Pour point (° C.) |  | −42 | −45 | −21 | −48 | −57 |
| Kv 100° C. (cS) | 86.69 | 25.41 | 6.53 | 77.73 | 5.4 | 5.8 |
| Kv 40° C. (cS) | 2360.73 | 261.94 | 38.86 | 2010.12 | 30.15 | 31 |
| VI | 91 | 116 | 121 | 96 | 114 | 138 |
| Wt % Noack volatility |  |  |  |  | 5.5 | 6-9 |

The lube product from Example 1-3 showed excellent viscometrics, good VI and very low pour points. Furthermore, the lube in Example 3 showed lower Noack volatility of 5.5% than the synthetic poly-alpha-olefin lube of 5.8 cSt. The Example 1-3 lubes are derived from natural resources and can be made by efficient processes and have lube properties comparable to synthetic lube base stocks made from PAOs.

Both the starting material (Unidyme 10) and the products in Example 3 were analyzed using mass spectroscopy. The starting material was analyzed using Field Desorption Mass Spectroscopy (FDMS) and the products by Field Ionization Mass Spectroscopy (FIMS). Major species are listed in Table 4 below. The term DBE refers to double bond equivalent, indicating the degree of unsaturation for a given hydrocarbon molecule compared with the fully saturated hydrocarbon formula $C_nH_{2n+2}$ (n is an integer). By definition, a hydrocarbon molecule containing one C=C double bond ($C_nH_{2n}$) has a DBE of one. A hydrocarbon molecule containing one naphthenic ring but otherwise saturated ($C_nH_{2n}$) has a DBE of one. Similarly, the double bond equivalent can also be defined for the acid dimer. In this case, the degree of unsaturation for a given dicarboxylic acid is compared with a fully saturated dicarboxylic acid with the formula $C_nH_{2n-2}O_4$, which only refers to the hydrocarbon fragment of the molecule and excludes the C=O bond in the carboxylic group.

TABLE 4

(Composition of feed and products for Example 3)

| Unidyme 10 | | | | Product | | | |
|---|---|---|---|---|---|---|---|
| Mass | Percent | Formula | DBE ex. C=O | Mass | Percent | Formula | DBE |
| 562 | 53 | $C_{36}H_{66}O_4$ | 2 | 476 | 37.2 | $C_{34}H_{68}$ | 1 |
| 564 | 18 | $C_{36}H_{68}O_4$ | 1 | 478 | 6.7 | $C_{34}H_{70}$ | 0 |
| 560 | 12 | $C_{36}H_{64}O_4$ | 3 | 474 | 8.2 | $C_{34}H_{66}$ | 2 |
| 558 | 7 | $C_{36}H_{62}O_4$ | 4 | 472 | 1.8 | $C_{34}H_{64}$ | 3 |
| 556 | 6 | $C_{36}H_{60}O_4$ | 5 | 470 | 9.6 | $C_{34}H_{62}$ | 4 |
| 554 | 1.5 | $C_{36}H_{58}O_4$ | 6 | 468 | 9.1 | $C_{34}H_{60}$ | 5 |
| Sub-total | 97.5 | | | Sub-total | 72.6 | | |
| | | | | 504 | 0.6 | $C_{36}H_{72}$ | 1 |
| | | | | 492 | 0.4 | $C_{35}H_{72}$ | 0 |
| | | | | 490 | 2.5 | $C_{35}H_{70}$ | 1 |
| | | | | 488 | 1.3 | $C_{35}H_{68}$ | 2 |
| | | | | 462 | 4.7 | $C_{33}H_{66}$ | 1 |
| | | | | 460 | 1.2 | $C_{33}H_{64}$ | 2 |
| | | | | 456 | 1.4 | $C_{33}H_{60}$ | 4 |
| | | | | 454 | 1.6 | $C_{33}H_{58}$ | 5 |
| | | | | 448 | 2.3 | $C_{32}H_{64}$ | 1 |
| | | | | 434 | 1.6 | $C_{31}H_{62}$ | 1 |
| | | | | 420 | 1.3 | $C_{30}H_{60}$ | 1 |
| | | | | 406 | 1.1 | $C_{29}H_{58}$ | 1 |
| | | | | 392 | 1 | $C_{28}H_{56}$ | 1 |
| | | | | 378 | 1 | $C_{27}H_{54}$ | 1 |
| | | | | Subtotal | 22 | | |
| Others | 2.5 | | | Others | 5.4 | | |

By comparing the major components in the starting material and the products, the difference in mass for the corresponding pairs is 86. Thus, the major reaction is hydro-decarboxylation, wherein the oxygen atoms in the starting material are removed in the form of $CO_2$ and the C=C double bond is saturated by hydrogen. Therefore both the saturation for the hydrocarbon fragment and the oxygen removal are achieved in a substantially single step.

Figure 11:
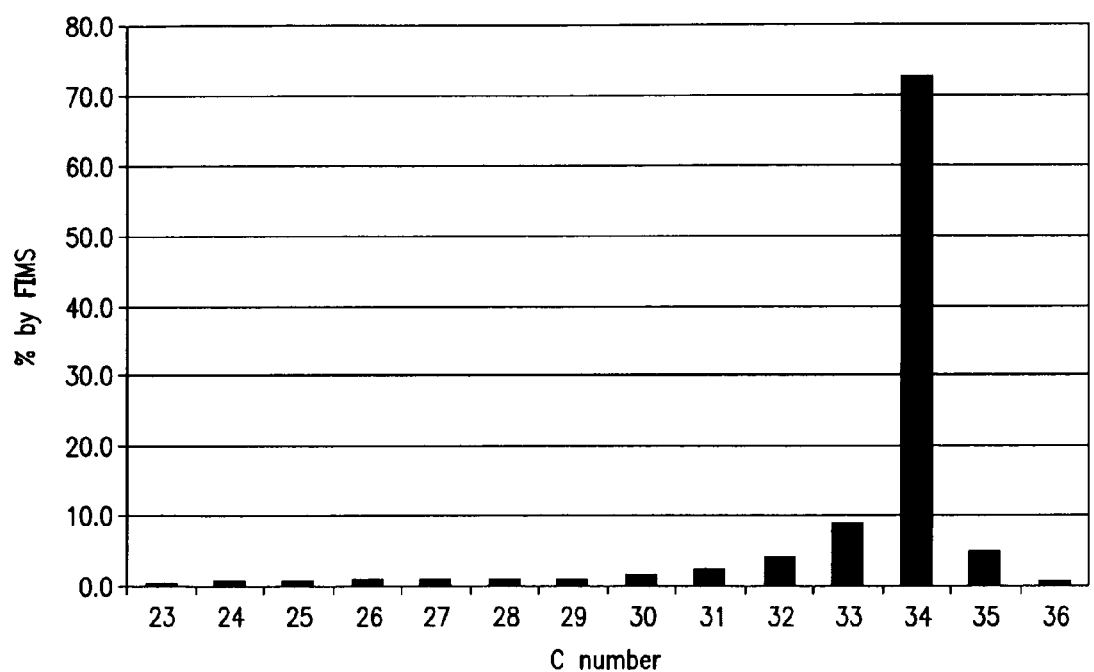
FIG. 11 is the carbon number distribution for products from Example 3.

The composition for the products in Example 3 is illustrated in FIG. 11 below. The products contain predominantly components with 34 carbon atoms. In those products, two carbons were lost during the hydrogenation step.

Applicants have attempted to disclose all embodiments and applications of the disclosed subject matter that could be reasonably foreseen. However, there may be unforeseeable, insubstantial modifications that remain as equivalents. While the present disclosure has been described in conjunction with specific, exemplary embodiments thereof, it is evident that many alterations, modifications, and variations will be apparent to those skilled in the art in light of the foregoing description without departing from the spirit or scope of the present disclosure. Accordingly, the present disclosure is intended to embrace all such alterations, modifications, and variations of the above detailed description.

All patents, test procedures, and other documents cited herein, including priority documents, are fully incorporated by reference to the extent such disclosure is not inconsistent with this disclosure and for all jurisdictions in which such incorporation is permitted.

When numerical lower limits and numerical upper limits are listed herein, ranges from any lower limit to any upper limit are contemplated.

What is claimed is:

1. A process for making one or more saturated hydrocarbons comprising:
    oligomerizing one or more unsaturated carboxylic acids having from 4 to 38 carbon atoms in the presence of a solid acid catalyst to form one or more unsaturated oligomeric acids including less than 90% by weight of cyclic oligomers, and
    hydrogenating the one or more unsaturated oligomeric acids via contact with hydrogen in the presence of a hydrogenation catalyst to form one or more saturated hydrocarbons,
    and
    wherein the solid acid catalyst is an amorphous aluminosilicate.

2. The process of claim 1, wherein the oligomerizing step includes dimerization.

3. The process of claim 1, wherein the one or more unsaturated oligomeric acids includes from 18 to 180 carbons.

4. The process of claim 1, wherein the one or more unsaturated carboxylic acids includes from 12 to 24 carbon atoms derived from biological based sources, petroleum based sources or combinations thereof.

5. The process of claim 1, wherein the one or more unsaturated carboxylic acids includes at least 20% by weight of mono-unsaturated fatty acids.

6. The process of claim 5, wherein the one or more unsaturated carboxylic acids includes at least 30% by weight of mono-unsaturated fatty acids.

7. The process of claim 6, wherein the one or more unsaturated carboxylic acids includes at least 70% by weight of mono-unsaturated fatty acids.

8. The process of claim 1, wherein the oligomerizing step is with a hydrocarbon feedstock having a mono-unsaturation content of at least 30 wt %.

9. The process of claim 8, wherein the oligomerizing step is with a hydrocarbon feedstock having a mono-unsaturation content of at least 70 wt %.

10. The process of claim 1, wherein the one or more unsaturated oligomeric acids includes less than 50% by weight of cyclic oligomers.

11. The process of claim 1, wherein the oligomerizing step is carried out at 50° C. to 350° C.

12. The process of claim 11, wherein the oligomerizing step is carried out at 100° C. to 250° C.

13. The process of claim 12, wherein the oligomerizing step is carried out at 100° C. to 200° C.

14. The process of claim 1, wherein the oligomerizing step is carried out at up to 500 psi.

15. The process of claim 14, wherein the oligomerizing step is carried out at up to 150 psi.

16. The process of claim 1, wherein the oligomerizing step is carried out in the presence of hydrogen.

17. The process of claim 1, wherein the oligomerizing step is carried out in batch mode.

18. The process of claim 1, wherein the oligomerizing step is carried out in CSTR mode.

19. The process of claim 1, wherein the oligomerizing step is carried out in a fixed bed reactor.

20. The process of claim 1, wherein the oligomerizing step is carried out for a residence time of 5 minutes to 50 hours.

21. The process of claim 20, wherein the oligomerizing step is carried out for a residence time of 20 minutes to 10 hours.

22. The process of claim 21, wherein the oligomerizing step is carried out for a residence time of 30 minutes to 5 hours.

23. The process of claim 1, wherein the oligomerizing step is carried out at a weight hourly space velocity of 0.2 grams to 50 grams of feed per gram of catalyst.

24. The process of claim 23, wherein the oligomerizing step is carried out at a weight hourly space velocity of 0.3 grams to 10 grams of feed per gram of catalyst.

25. The process of claim 1, wherein the oligomerizing step is carried out at a conversion level of at least 10 mole percent.

26. The process of claim 1, wherein the oligomerizing step is carried out at a conversion level of 20 to 90 mole percent.

27. The process of claim 1, wherein the hydrogenation catalyst is selected from Mo, Re, Fe, Ru, Co, Rh, Ir, Ni, Pd, Pt, Cu, Zn, and combinations thereof.

28. The process of claim 27, wherein the hydrogenation catalyst is supported on a support selected from silica, alumina, zirconia, clays, Kieselguhr, amorphous aluminosilicates, and zeolites.

29. The process of claim 1, wherein the hydrogenating step is carried out at 100° C. to 500° C.

30. The process of claim 29, wherein the hydrogenating step is carried out at 200° C. to 400° C.

31. The process of claim 30, wherein the hydrogenating step is carried out at 250° C. to 350° C.

32. The process of claim 1, wherein the hydrogenating step is carried out at least at 300 psi.

33. The process of claim 32, wherein the hydrogenating step is carried out at least at 400 psi.

34. The process of claim 1, wherein the hydrogenating step is carried out in batch mode.

35. The process of claim 1, wherein the hydrogenating step is carried out in CSTR mode.

36. The process of claim 1, wherein the hydrogenating step is carried out in a fixed bed reactor.

37. The process of claim 1, wherein the hydrogenating step is carried out for a residence time of 5 minutes to 50 hours.

38. The process of claim 37, wherein the hydrogenating step is carried out for a residence time of 10 minutes to 10 hours.

* * * * *